(12) United States Patent
Verdino et al.

(10) Patent No.: US 11,859,005 B2
(45) Date of Patent: Jan. 2, 2024

(54) GITR ANTAGONISTS AND METHODS OF USING THE SAME

(71) Applicant: Eli Lilly and Company, Indianapolis, IN (US)

(72) Inventors: Petra Verdino, San Diego, CA (US); Paul Francis Cain, Greenwood, IN (US); Melinda Ann Lacerte, San Diego, CA (US); Stacey Lynn Lee, San Diego, CA (US); Mark Andrew Wortinger, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/590,135

(22) Filed: Feb. 1, 2022

(65) Prior Publication Data

US 2022/0251227 A1    Aug. 11, 2022

Related U.S. Application Data

(60) Provisional application No. 63/297,968, filed on Jan. 10, 2022, provisional application No. 63/144,732, filed on Feb. 2, 2021.

(51) Int. Cl.
*C07K 16/28* (2006.01)
*C12N 15/63* (2006.01)

(52) U.S. Cl.
CPC .......... *C07K 16/2878* (2013.01); *C12N 15/63* (2013.01); *C07K 2317/565* (2013.01)

(58) Field of Classification Search
CPC .......... C07K 16/2878; C07K 2317/565; C12N 15/63; A61K 2039/505
See application file for complete search history.

(56) References Cited

U.S. PATENT DOCUMENTS

| | | | |
|---|---|---|---|
| 9,309,321 B2 | 4/2016 | Kwon | |
| 2013/0108641 A1 | 5/2013 | Baurin et al. | |
| 2014/0348841 A1 | 11/2014 | Schebye et al. | |
| 2017/0088620 A1* | 3/2017 | Nioi | A61K 39/3955 |

FOREIGN PATENT DOCUMENTS

| | | |
|---|---|---|
| WO | 2013/039954 A1 | 3/2013 |
| WO | 2015/184099 A1 | 12/2015 |
| WO | 2017/096179 A1 | 6/2017 |
| WO | 2017/096189 A1 | 6/2017 |
| WO | 2017/096276 A1 | 6/2017 |
| WO | 2018/089628 A1 | 5/2018 |
| WO | 2018/170288 A1 | 9/2018 |
| WO | WO-2018176159 A1 * | 10/2018 ............ A61K 35/17 |

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*
Nishioka, et al., "In vivo expansion of CD4+Foxp3+ regulatory T cells mediated by GITR molecules". Immunology Letters 121 (Jul. 17, 2008) 97-104.
Snell, L.M., et al., "CD8 T Cell-Intrinsic GITR Is Required for T Cell Clonal Expansion and Mouse Survival following Severe Influenza Infection" Nov. 12, 2010 J. Immunol., 185(12):7223-7234.
Gonzalez, Ana M., et al., AACR Annual Meeting 2017; Apr. 1-5, 2017, Washington, DC, Abstract 3643 INCAGN1876, a unique GITR agonist antibody that facilitates GITR oligomerization.
Siu, et al., "Preliminary Results of a Phase 1/2a Study of BMS-986156 (glucocorticoid-induced tumor necrosis factor receptor-related gene [GITR] agonist) Alone and in Combination With Nivolumab in Patients With Advanced Solid Tumors"., ASCO Annual Meeting Jun. 2017 Poster.
Ravit, et al, "First-in-human phase 1 study of MK-1248, an anti-human glucocorticoid-induced tumor necrosis factor receptor (GITR) monoclonal antibody, as monotherapy or in combination with pembrolizumab in patients with advanced solid tumors." J Clin Oncol 36, Jun. 4, 2018 (suppl; abstr 3029). Poster Session (Board #243).
Chan, et al., "In vitro funcational activityof OMP-336B11, a GITRL-Fc fusion protein, on primary human immune cells"., OncoMed Pharmaceuticals, Poster Presentation, AACR Annual Meeting, Jul. 1, 2018.
Pedros, C., Altman, A., and Kong, K. "Role of TRAFs in Signaling Pathways Controlling T Follicular Helper Cell Differentiation and T Cell-Dependent Antibody Responses" Oct. 22, 2018, Front. Immunol. 9:2412.
Wang, et al., "Combination cancer immunotherapy targeting PD-1 and GITR can rescue CD8+ T cell dysfunction and maintain memory phenotype". Sci. Immunol. 3, eaat7061 (2018) Nov. 2, 2018.
Zappasodi, et al., "Rational design of anti-GITR-based combination immunotherapy"., Nature Medicine 25, 759-766 (2019).
Tian, J., et al., "The Role of GITR/GITRL Interaction in Autoimmune Diseases" Front. Immunol., 11:1-7, Oct. 9, 2020.

* cited by examiner

*Primary Examiner* — Adam Weidner
*Assistant Examiner* — Laura Ann Essex
(74) *Attorney, Agent, or Firm* — Robert L. Sharp

(57) ABSTRACT

The present disclosure relates to compounds that bind to human GITR, pharmaceutical compositions comprising such compounds, and methods of using such compounds.

17 Claims, No Drawings

Specification includes a Sequence Listing.

SEQUENCE LISTING

```
<160> NUMBER OF SEQ ID NOS: 22

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Ala Ala Ser Gly Tyr Thr Phe Ser Ser Tyr Val Met His
1               5                   10

<210> SEQ ID NO 2
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 2

Val Thr Ser Tyr Asp Gly Thr His Glu Tyr
```

<210> SEQ ID NO 3
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 3

Ala Arg Glu Asn Asn Trp Ala Pro Asp Tyr
 1               5                  10

<210> SEQ ID NO 4
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 4

Arg Ala Ser Gln Asp Ile Ser Asn Ser Leu Ala
 1               5                  10

<210> SEQ ID NO 5
<211> LENGTH: 8
<212> TYPE: PRT
<213> ORGANISM: ARTIFICIAL SEQUENCE
<220> FEATURE:
<223> OTHER INFORMATION: Synthetic Construct

<400> SEQUENCE: 5

Tyr Ala Ala Phe Ser Leu Gln Ser
 1               5

<210> SEQ ID NO 6
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 6

Tyr Gln Tyr Tyr Asn Tyr Pro Ser Ala
 1               5

<210> SEQ ID NO 7
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 7

Val Thr Ser Tyr Asp Gly Thr His Glu Leu
 1               5                  10

<210> SEQ ID NO 8
<211> LENGTH: 117
<212> TYPE: PRT
<213> ORGANISM: ARTIFICIAL SEQUENCE
<220> FEATURE:
<223> OTHER INFORMATION: Synthetic Construct

<400> SEQUENCE: 8

Gln Val Gln Leu Val Glu Ser Gly Gly Gly Val Val Gln Pro Gly Arg
 1               5                  10                  15

Ser Leu Arg Leu Ser Cys Ala Ala Ser Gly Tyr Thr Phe Ser Ser Tyr
            20                  25                  30

Val Met His Trp Val Arg Gln Ala Pro Gly Lys Gly Leu Glu Trp Val
        35                  40                  45

Ala Val Thr Ser Tyr Asp Gly Thr His Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Asn Trp Ala Pro Asp Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: ARTIFICIAL SEQUENCE
<220> FEATURE:
<223> OTHER INFORMATION: Synthetic Construct

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Val Met His Trp Val Arg Gln Ala Pro Gly Lys Gly Leu Glu Trp Val
        35                  40                  45

Ala Val Thr Ser Tyr Asp Gly Thr His Glu Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Asn Trp Ala Pro Asp Tyr Trp Gly Gln Gly Thr Leu
            100                 105                 110

Val Thr Val Ser Ser
        115

<210> SEQ ID NO 10
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Ser
            20                  25                  30

Leu Ala Trp Tyr Gln Gln Lys Pro Gly Lys Ala Pro Lys Arg Leu Ile
        35                  40                  45

Tyr Ala Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
Glu Asp Phe Ala Thr Tyr Tyr Cys Tyr Gln Tyr Tyr Asn Tyr Pro Ser
                        85                  90                  95

Ala Phe Gly Gln Gly Thr Lys Leu Glu Ile Lys
                100                 105

<210> SEQ ID NO 11
<211> LENGTH: 30
<212> TYPE: PRT
<213> ORGANISM: ARTIFICIAL SEQUENCE
<220> FEATURE:
<223> OTHER INFORMATION: Synthetic Construct

<400> SEQUENCE: 11

Asp Lys Thr His Thr Gly Gly Gly Gln Gly Gly Gly Gly Gln Gly
1               5                   10                  15

Gly Gly Gln Gly Gly Gly Gly Gln Gly Gly Gly Gly Gln
            20                  25                  30

<210> SEQ ID NO 12
<211> LENGTH: 28
<212> TYPE: PRT
<213> ORGANISM: ARTIFICIAL SEQUENCE
<220> FEATURE:
<223> OTHER INFORMATION: Synthetic Construct

<400> SEQUENCE: 12

Asp Lys Thr Gly Gly Gly Gln Gly Gly Gly Gln Gly Gly
1               5                   10                  15

Gly Gln Gly Gly Gly Gln Gly Gly Gly Gln
            20                  25

<210> SEQ ID NO 13
<211> LENGTH: 128
<212> TYPE: PRT
<213> ORGANISM: ARTIFICIAL SEQUENCE
<220> FEATURE:
<223> OTHER INFORMATION: Synthetic Construct

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
                20                  25                  30

Ala Val Ala Trp Phe Arg Gln Ala Pro Gly Lys Gly Arg Glu Phe Val
            35                  40                  45

Ala Gly Ile Gly Gly Gly Val Asp Ile Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Pro
        115                 120                 125

<210> SEQ ID NO 14
<211> LENGTH: 378
<212> TYPE: PRT
<213> ORGANISM: Artificial Sequence
```

<220> FEATURE:
<223> OTHER INFORMATION: Synthetic Construct

<400> SEQUENCE: 14

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Val Met His Trp Val Arg Gln Ala Pro Gly Lys Gly Leu Glu Trp Val
        35                  40                  45

Ala Val Thr Ser Tyr Asp Gly Thr His Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Asn Trp Ala Pro Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Gly Gly Gly Gly Gln Gly Gly Gly Gln Gly Gly Gly Gly Gln
225                 230                 235                 240

Gly Gly Gly Gly Gln Gly Gly Gly Gln Glu Val Gln Leu Leu Glu
                245                 250                 255

Ser Gly Gly Gly Leu Val Gln Pro Gly Gly Ser Leu Arg Leu Ser Cys
            260                 265                 270

Ala Ala Ser Gly Arg Tyr Ile Asp Glu Thr Ala Val Ala Trp Phe Arg
    275                 280                 285

Gln Ala Pro Gly Lys Gly Arg Glu Phe Val Ala Gly Ile Gly Gly Gly
290                 295                 300

Val Asp Ile Thr Tyr Tyr Ala Asp Ser Val Lys Gly Arg Phe Thr Ile
305                 310                 315                 320

Ser Arg Asp Asn Ser Lys Asn Thr Leu Tyr Leu Gln Met Asn Ser Leu
                325                 330                 335

Arg Pro Glu Asp Thr Ala Val Tyr Tyr Cys Ala Ala Arg Pro Gly Arg
            340                 345                 350

Pro Leu Ile Thr Ser Lys Val Ala Asp Leu Tyr Pro Tyr Trp Gly Gln
    355                 360                 365

Gly Thr Leu Val Thr Val Ser Ser Pro Pro
370                 375
```

<210> SEQ ID NO 15

<211> LENGTH: 378
<212> TYPE: PRT
<213> ORGANISM: ARTIFICIAL SEQUENCE
<220> FEATURE:
<223> OTHER INFORMATION: Synthetic Construct

<400> SEQUENCE: 15

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Val Met His Trp Val Arg Gln Ala Pro Gly Lys Gly Leu Glu Trp Val
        35                  40                  45

Ala Val Thr Ser Tyr Asp Gly Thr His Glu Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Asn Trp Ala Pro Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Gly Gly Gly Gly Gln Gly Gly Gly Gln Gly Gly Gly Gln
225                 230                 235                 240

Gly Gly Gly Gly Gln Gly Gly Gly Gln Glu Val Gln Leu Leu Glu
                245                 250                 255

Ser Gly Gly Gly Leu Val Gln Pro Gly Gly Ser Leu Arg Leu Ser Cys
            260                 265                 270

Ala Ala Ser Gly Arg Tyr Ile Asp Glu Thr Ala Val Ala Trp Phe Arg
    275                 280                 285

Gln Ala Pro Gly Lys Gly Arg Glu Phe Val Ala Gly Ile Gly Gly Gly
    290                 295                 300

Val Asp Ile Thr Tyr Tyr Ala Asp Ser Val Lys Gly Arg Phe Thr Ile
305                 310                 315                 320

Ser Arg Asp Asn Ser Lys Asn Thr Leu Tyr Leu Gln Met Asn Ser Leu
                325                 330                 335

Arg Pro Glu Asp Thr Ala Val Tyr Tyr Cys Ala Ala Arg Pro Gly Arg
            340                 345                 350

Pro Leu Ile Thr Ser Lys Val Ala Asp Leu Tyr Pro Tyr Trp Gly Gln
        355                 360                 365

Gly Thr Leu Val Thr Val Ser Ser Pro Pro
    370                 375
```

<210> SEQ ID NO 16
<211> LENGTH: 214
<212> TYPE: PRT
<213> ORGANISM: ARTIFICIAL SEQUENCE
<220> FEATURE:
<223> OTHER INFORMATION: Synthetic Construct

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Ser
            20                  25                  30

Leu Ala Trp Tyr Gln Gln Lys Pro Gly Lys Ala Pro Lys Arg Leu Ile
        35                  40                  45

Tyr Ala Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Tyr Gln Tyr Tyr Asn Tyr Pro Ser
                85                  90                  95

Ala Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 1134
<212> TYPE: DNA
<213> ORGANISM: ARTIFICIAL SEQUENCE
<220> FEATURE:
<223> OTHER INFORMATION: Synthetic Construct

<400> SEQUENCE: 17

```
caagtgcagc tcgtggagtc gggtggcgga gtggtgcagc ccggaaggtc cttgcggctc     60
tcctgtgccg cttccggcta caccttctcg agctacgtga tgcactgggt cagacaggca    120
ccgggaaagg gtctggaatg ggtggccgtg acttcctacg acggcaccca cgagtattac    180
gccgactcag tgaagggccg cttcactatc tcccgggaca actcaaagaa caccctgtat    240
ctgcaaatga actcactgcg ggccgaggac actgccgtgt actactgcgc gcgcgaaaac    300
aactgggccc ctgactactg gggacagggg actctggtca ctgtgtcgtc cgcctcgacc    360
aagggaccct ccgtgtttcc gctggcgcca agcagcaaga gcacctcggg gggaactgca    420
gccttggggt gcctcgtgaa ggattacttc cccgaaccag tgaccgtgtc ctggaactct    480
```

| | |
|---|---|
| ggggccctca ccagtggagt gcacactttc cctgcggtgc tgcagtcctc cggactgtac | 540 |
| agcctgtcca gcgtggtcac ggtgcccagc tcctcactgg cacccagac ctacatttgc | 600 |
| aacgtgaacc ataagccgtc caataccaaa gtcgataaga aagtcgagcc gaagtcctgc | 660 |
| gacaagacac acaccggtgg aggaggccag ggtggaggtg gacaaggcgg cggaggtcaa | 720 |
| ggcggaggag gacagggtgg cggaggacag gaagtgcagc tgctggagtc cggggggcgga | 780 |
| ctggtgcagc ctggcggatc attgcggctg tcgtgcgcgg cctccggacg ctacatcgac | 840 |
| gagacagcag tggcctggtt cagacaggct cccggaaagg gaagagagtt cgtggccgga | 900 |
| attggcgggg gagtcgacat tacctactac gccgattccg tgaagggtcg ctttaccatc | 960 |
| tcccgggaca attcgaagaa caccctgtac ctccaaatga actcgctgag gccggaagat | 1020 |
| accgcggtgt attactgtgc cgcccgcccg ggacgcccgc tgatcacgtc caaagtcgcc | 1080 |
| gacctgtacc cgtactgggg acagggtacc ctcgtgaccg tgtccagccc tccc | 1134 |

<210> SEQ ID NO 18
<211> LENGTH: 1134
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| caggtgcagc tcgtggagtc gggtggcgga gtggtgcagc ccggaaggtc cttgcggctc | 60 |
| tcctgtgccg cttccggcta caccttctcg agctacgtga tgcactgggt cagacaggca | 120 |
| ccaggaaagg gtctggaatg ggtggccgtg acctcctacg acggcaccca cgagctgtac | 180 |
| gccgactcag tgaagggccg cttcactatc tcccgggaca actcaaagaa caccctgtat | 240 |
| ctgcaaatga actcactgcg ggccgaggac actgccgtgt actactgcgc gcgcgaaaat | 300 |
| aactgggccc ctgactactg gggacagggg actctggtca ctgtgtcgtc cgcctcgacc | 360 |
| aagggacccct ccgtgtttcc gctggcgcca agcagcaaga gcacctcggg gggaactgca | 420 |
| gccttggggt gcctcgtgaa ggattacttc cccgaaccag tgaccgtgtc ctggaactct | 480 |
| ggggcccctca ccagtggagt gcacactttc cctgcggtgc tgcagtcctc cggactgtac | 540 |
| agcctgtcca gcgtggtcac ggtgcccagc tcctcactgg cacccagac ctacatttgc | 600 |
| aacgtgaacc ataagccgtc caataccaaa gtcgataaga aagtcgagcc gaagtcctgc | 660 |
| gacaagacac acaccggtgg aggaggccag ggtggaggtg gacaaggcgg cggaggtcaa | 720 |
| ggcggaggag gacagggtgg cggaggacag gaagtgcagc tgctggagtc cggggggcgga | 780 |
| ctggtgcagc ctggcggatc attgcggctg tcgtgcgcgg cctccggacg ctacatcgac | 840 |
| gagacagcag tggcctggtt cagacaggct cccggaaagg gaagagagtt cgtggccgga | 900 |
| attggcgggg gagtcgacat tacctactac gccgattccg tgaagggtcg ctttaccatc | 960 |
| tcccgggaca attcgaagaa caccctgtac ctccaaatga actcgctgag gccggaagat | 1020 |
| accgcggtgt attactgtgc cgcccgcccg ggacgcccgc tgatcacgtc caaagtcgcc | 1080 |
| gacctgtacc cgtactgggg acagggtacc ctcgtgaccg tgtccagccc tccc | 1134 |

<210> SEQ ID NO 19
<211> LENGTH: 642
<212> TYPE: DNA
<213> ORGANISM: ARTIFICIAL SEQUENCE
<220> FEATURE:
<223> OTHER INFORMATION: Synthetic Construct

<400> SEQUENCE: 19

```
gatatccaga tgacccagtc cccgagctcg ctgtccgctt ccgtgggaga cagagtgacg      60
atcacttgtc gggccagcca agacattagc aactccctgg cctggtacca gcagaagccc     120
ggcaaagcac ccaagaggtt gatctacgcg gccttttcac tgcaatccgg agtgccgagc     180
cggttctccg gatccggttc agggaccgag ttcaccttga ccattagcag cctgcagccc     240
gaagatttcg ccacttacta ctgctaccag tattacaatt acccatcggc gttcggccaa     300
ggcaccaagc tcgagatcaa gcggaccgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcaagtcac ccatcagggc      600 ctgagctcgc ccgtcacaaa gagcttcaac aggggagagt gc                       642
```

<210> SEQ ID NO 20
<211> LENGTH: 216
<212> TYPE: PRT
<213> ORGANISM: Homo sapiens

<400> SEQUENCE: 20

```
Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
        50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Leu Gly Trp Leu Thr Val Val
    130                 135                 140

Leu Leu Ala Val Ala Ala Cys Val Leu Leu Leu Thr Ser Ala Gln Leu
145                 150                 155                 160

Gly Leu His Ile Trp Gln Leu Arg Ser Gln Cys Met Trp Pro Arg Glu
                165                 170                 175

Thr Gln Leu Leu Leu Glu Val Pro Pro Ser Thr Glu Asp Ala Arg Ser
            180                 185                 190

Cys Gln Phe Pro Glu Glu Glu Arg Gly Glu Arg Ser Ala Glu Glu Lys
        195                 200                 205

Gly Arg Leu Gly Asp Leu Trp Val
    210                 215
```

<210> SEQ ID NO 21
<211> LENGTH: 136
<212> TYPE: PRT
<213> ORGANISM: Homo sapiens

```
<400> SEQUENCE: 21

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
    50              55                  60

Arg His His Pro Cys Pro Pro Gly Gln Gly Val Gln Ser Gln Gly Lys
65              70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
                100                 105                 110

Gly Phe Leu Thr Val Phe Pro Gly Asn Lys Thr His Asn Ala Val Cys
            115                 120                 125

Val Pro Gly Ser Pro Pro Ala Glu
    130                 135

<210> SEQ ID NO 22
<211> LENGTH: 20
<212> TYPE: PRT
<213> ORGANISM: Artificial Sequence
<220> FEATURE:
<223> OTHER INFORMATION: Synthetic Construct

<400> SEQUENCE: 22

Met Glu Thr Asp Thr Leu Leu Leu Trp Val Leu Leu Leu Trp Val Pro
1               5                   10                  15

Gly Ser Thr Gly
            20
```

GITR ANTAGONISTS AND METHODS OF USING THE SAME

The disclosure relates generally to biology and medicine, and more particularly it relates to antagonists of glucocorticoid-induced TNFR-related protein (GITR), also known as tumor necrosis factor receptor superfamily member 18 (TNFRSF18), especially monovalent antagonist formats that lack Fc-gamma receptor (FcγR) binding and are unable to stimulate GITR agonism. The disclosure further relates to compositions including the same and their use in treating autoimmune diseases or disorders.

GITR is a member of the TNFR superfamily and is known to be expressed on various immune cells including regulatory T cells (Tregs) and activated T cells. See, e.g., Tian, J., et al., (2020) *Front. Immunol.*, 11:1-7. GITR is a single-pass type I transmembrane protein and its extracellular domain (ECD) consists of three cysteine-rich domains, which are typical of the TNFR superfamily.

GITR is multimerized and activated upon interaction with its trimerized ligand GITRL (TNFSF18) resulting in induction of NFkB activation through TRAF2/TRAF5. See, e.g., Pedros, C., Altman, A., and Kong, K. (2018) *Front. Immunol.* 9:2412; and Snell, L. M., et al., (2010) *J.Immunol.*, 185(12):7223-7234. The consequences of GITRL-induced GITR signaling include co-stimulation of T cell proliferation and cytokine release as well as abrogation of Treg suppressive effects. It has also been shown that GITR can be agonized through antibody binding and that this GITR activation may be further enhanced by agonist antibody or GITRL-Fc binding to FcγR; this enhancement is thought to be mediated by increased avidity or receptor multimerization. Therefore, a GITR antagonist is likely to exhibit agonist activity if it is bound on a surface, perhaps through binding FcγRs on a cell surface, resulting in multimerization of GITR and subsequent activation. Thus, a monovalent anti-GITR antibody fragment that efficiently blocks GITRL binding to its receptor and prevents receptor activation without the ability to substantially engage FcγRs is desired. The most straightforward way to ensure there is no possibility of FcγR engagement is to generate antibody fragments that are entirely devoid of the Fc domain. However, antibody fragments that are entirely devoid of the Fc domain, such as Fabs, are known to have a short half-life (t½), which presents challenges when using it as a therapeutic agent.

Several strategies exist for extending the t½ of biotherapeutics, which can improve their pharmacokinetic (PK) and/or pharmacodynamic (PD) profiles. Such strategies typically use bulking moieties or neonatal Fc receptor (FcRn)-mediated recycling. In this manner, antibodies (Abs) or fragments thereof (e.g., Fab, Fc, etc.); polymers such as polyethylene glycol (PEG), polysialic acid (PSA), hyaluronic acid (HA) and hydroxy-ethyl-starch (HES); fatty acids and other lipids; N- or O-glycosylation; and serum albumin or other plasma proteins (such as transferrin), can be covalently and/or non-covalently bound to a given biotherapeutic to extend its half-life.

International Patent Application published under the Patent Cooperation Treaty (PCT) as WO 2017/096189 (Agenus) discloses, inter alia, anti-human GITR antagonist antibodies (including, but not limited to, bispecific antibodies, e.g., antibodies that comprise a first antigen-binding domain that binds to human GITR, and a second antigen-binding domain that doesn't specifically bind to an antigen expressed by a human immune cell), as well as methods of using them. In some embodiments, and in certain in vitro assays, certain anti-human GITR antibodies disclosed in WO 2017/096189 behave as antagonists. However, later reports published by the applicant Agenus describe INCAGN1876, also known as ragifilimab, as being an agonist antibody for GITR. See, e.g., Gonzalez, Ana M., et al., AACR Annual Meeting 2017; April 1-5, 2017; Washington, DC, Abstract 3643.

Thus, there still exists a need for anti-human GITR antibodies that 1) bind human GITR with desirable association and dissociation rates for optimal antagonistic activity, 2) block GITRL binding to GITR and prevent GITR activation, 3) lack detectable stimulation of human GITR, 4) have sufficient pharmacokinetic (PK) and/or pharmacodynamic (PD) profiles and demonstrable in vivo efficacy as an monotherapy for the treatment and/or prevention of autoimmune disorders, allergic disease, asthma, atopic dermatitis (AtD), joint inflammation, arthritis, rheumatoid arthritis (RA), or other inflammatory disorders such as, inflammatory bowel disease (IBD), Crohn's disease (CD) and/or ulcerative colitis (UC), 5) cause no significant induction of cytokine release, 6) have low immunogenicity (i.e., sufficiently non-immunogenic in cynomolgus monkeys and/or humans), and 7) demonstrate in vitro and in vivo physical and chemical stability including, but not limited to, thermal stability, solubility, low self-association, and pharmacokinetic characteristics which are acceptable for development and/or use in the treatment of autoimmune disorders, allergic disease, asthma, AtD, joint inflammation, arthritis, RA, or other inflammatory disorders such as, IBD, CD and/or UC.

Accordingly, the present invention provides novel human GITR antagonist compounds that 1) bind human GITR with desirable association and dissociation rates for optimal antagonistic activity, 2) block GITRL binding to GITR and prevent GITR activation, 3) lack detectable stimulation of human GITR 4) have sufficient pharmacokinetic (PK) and/or pharmacodynamic (PD) profiles and demonstrable in vivo efficacy as an monotherapy for the treatment and/or prevention of autoimmune disorders, allergic disease, asthma, atopic dermatitis, joint inflammation, arthritis, rheumatoid arthritis, or other inflammatory disorders such as, IBD, CD and/or UC, 5) cause no significant induction of cytokine release, 6) have low immunogenicity (i.e., sufficiently non-immunogenic in cynomolgus monkeys and/or humans), and 7) demonstrate in vitro and in vivo physical and chemical stability including, but not limited to, thermal stability, solubility, low self-association, and pharmacokinetic characteristics which are acceptable for development and/or use in the treatment of autoimmune disorders, allergic disease, asthma, AtD, joint inflammation, arthritis, RA, or other inflammatory disorders such as, IBD, CD and/or UC.

The present disclosure provides compounds comprising an anti-human GITR antigen binding fragment comprising: 1) a heavy chain variable region (HCVR) comprising an HCDR1 having the amino acid sequence of SEQ ID NO: 1, an HCDR2 having the amino acid sequence of SEQ ID NO: 2 or 7, an HCDR3 having the amino acid sequence of SEQ ID NO: 3; and 2) a light chain variable region (LCVR) comprising an LCDR1 having the amino acid sequence of SEQ ID NO: 4, an LCDR2 having the amino acid sequence of SEQ ID NO: 5, and an LCDR3 having the amino acid sequence of SEQ ID NO: 6.

In some instances, the compounds herein are of the formula (from amino-terminus (N-terminus) to carboxy-terminus (C-terminus)): X-L-M (wherein the N-terminus of L is fused to the C-terminus of the HC of X and the C-terminus of L is fused to the N-terminus of M); or X-L-M (wherein the N-terminus of L is fused to the C-terminus of the LC of X and the C-terminus of L is fused to the N-terminus of M); or M-L-X (wherein the N-terminus of L is fused to the C-terminus of M and the C-terminus of L is fused to the N-terminus of the HC of X);); or M-L-X (wherein the N-terminus of L is fused to the C-terminus of M and the C-terminus of L is fused to the N-terminus of the LC of X); wherein M is a compound acting as a t½-extending moiety, L (if present) is a linker, and X is an antibody Fab fragment that binds human GITR. In some instances, M is an albumin-binding VHH, and L can have an amino acid sequence comprising (GGGGQ)$_n$, where n can be from 1 to 15, especially from about 4 to about 8. In other instances, M comprises an amino acid sequence as shown in SEQ ID NO: 13, and L can have an amino acid sequence selected from SEQ ID NOS:11 or 12. In still other instances, L can have one or more additions, deletions, insertions or substitutions such that L has an amino acid sequence having at least about 90% to about 99% sequence similarity to any one of SEQ ID NOS:11 or 12.

The disclosure also describes pharmaceutical compositions that include at least one compound herein and a pharmaceutically acceptable carrier.

Additionally, the disclosure describes methods of using the compounds and pharmaceutical compositions for medicaments.

Furthermore, the disclosure describes uses of the compounds herein in the manufacture of medicaments.

DETAILED DESCRIPTION

Unless defined otherwise, all technical and scientific terms used herein have the same meaning as commonly understood by one of skill in the art to which the disclosure pertains. Although any methods and materials similar to or equivalent to those described herein can be used in the practice or testing of the analogs, pharmaceutical compositions and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Definitions

As used herein, "about" means within a statistically meaningful range of a value or values such as, for example, a stated concentration, length, molecular weight, pH, sequence similarity, time frame, temperature, volume, etc. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more of receptors, "activity," "activate," "activating" and the like means a capacity of a compound, such as a fusion herein, to bind to and induce a response at the receptor(s), as measured using assays known in the art, such as the in vitro assays described below.

As used herein, "amino acid" means a molecule that, from a chemical standpoint, is characterized by a presence of one or more amine groups and one or more carboxylic acid groups and may contain other functional groups. As is known in the art, there is a set of twenty amino acids that are designated as standard amino acids and that can be used as building blocks for most of the peptides/proteins produced by any living being. The amino acid sequences in the disclosure contain the standard single letter or three letter codes for the twenty naturally occurring amino acids.

As used herein, "analog" means a compound, such as a synthetic peptide or polypeptide, that activates a target receptor and that elicits at least one in vivo or in vitro effect elicited by a native agonist for that receptor.

The term "antibody," as used herein, refers to an immunoglobulin molecule that binds an antigen. Embodiments of an antibody include a monoclonal antibody, polyclonal antibody, human antibody, humanized antibody, chimeric antibody, or conjugated antibody. The antibodies can be of any class (e.g., IgG, IgE, IgM, IgD, IgA) and any subclass (e.g., IgG1, IgG2, IgG3, IgG4). An exemplary antibody is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on the internet; see Lefranc et al., Nucleic Acids Res. 1999; 27:209-212). The North CDR definitions are used for the anti-human GITR antibodies described herein.

The term "antigen-binding fragment" refers to a portion of an antibody that retains the ability to specifically interact with an epitope of an antigen. Examples of antigen binding fragments include, but are not limited to, Fab or Fab'. A "Fab" fragment consists of an entire antibody light chain comprising the light chain variable region (VL) and the light chain constant region (CL), along with the heavy chain variable region (VH) and the heavy chain first constant domain (CH1). Each Fab fragment is monovalent with respect to antigen binding, i.e., it has a single antigen-binding site. A Fab' fragment differs from the Fab fragment by having a few additional residues at the carboxyl terminus of the CH1 domain including one or more residues from the antibody hinge region. A Fab or Fab' described herein can be a human Fab or Fab' or a chimeric Fab or Fab' that comprises a human CL and CH1.

The terms "bind" and "binds" as used herein are intended to mean, unless indicated otherwise, the ability of a protein or molecule to form a chemical bond or attractive interaction with another protein or molecule, which results in proximity of the two proteins or molecules as determined by common methods known in the art.

As used herein, "biotherapeutic" and the like means an amino acid- or nucleic acid-based compounds such as antibodies, coagulation factors, clotting factors, cytokines, enzymes, growth factors, hormones, and fragments thereof, having at least one therapeutic activity/applicability, as well as therapeutic DNA and/or RNA molecules.

As used herein, "conservative substitution" means a variant of a reference peptide or polypeptide that is identical to the reference molecule, except for having one or more conservative amino acid substitutions in its amino acid sequence. In general, a conservatively modified variant includes an amino acid sequence that is at least about 70%, 75%, 80%, 85%, 90%, 91%, 92%, 93%, 94%, 95%, 96%, 97%, 98% or 99% identical to a reference amino acid sequence. More specifically, a conservative substitution refers to substitution of an amino acid with an amino acid having similar characteristics (e.g., charge, side-chain size, hydrophobicity/hydrophilicity, backbone conformation and rigidity, etc.) and having minimal impact on the biological activity of the resulting substituted peptide or polypeptide. Conservative substitutions of functionally similar amino acids are well known in the art and thus need not be exhaustively described herein.

As used herein, "effective amount" means an amount or dose of one or more of the compounds herein, or a pharmaceutically acceptable salt thereof that, upon single or multiple dose administration to an individual in need thereof, provides a desired effect in such an individual under diagnosis or treatment (i.e., may produce a clinically measurable difference in a condition of the individual, for example, reduction in one or more clinical disease activity measures such as American College of Rheumatology (ACR) 20, ACR50, ACR70; Disease Activity Score (DAS); Psoriasis Area and Severity Index (PASI) 50, PASI75, PASI90, PASI100; Systemic Lupus erythematosus disease activity index (SLEDAI); Mayo Score Disease activity index (DAI); Crohn's disease activity index (CDAI); Geboes score (GS); Robarts Histopathology index (RHI); Atopic dermatitis Severity Index (ADSI); and EULAR Sjogren's syndrome disease activity index (ESSDAI)). An effective amount can be readily determined by one of skill in the art by using known techniques and by observing results obtained under analogous circumstances. In determining the effective amount for an individual, a number of factors are considered, including, but not limited to, the species of mammal, its size, age and general health, the specific disease or disorder involved, the degree of or involvement or the severity of the disease or disorder, the response of the individual, the particular compound administered, the mode of administration, the bioavailability characteristics of the preparation administered, the dose regimen selected, the use of concomitant medication, and other relevant circumstances.

As used herein, "extended duration of action" means that binding affinity and activity for a fusion including at least one compound herein and a biotherapeutic herein continues for a period of time greater than a native biotherapeutic, allowing for dosing at least as infrequently as once daily or even thrice-weekly, twice-weekly or once-weekly. The time action profile may be measured using known pharmacokinetic test methods such as those utilized in the Examples below.

The term "Fc region" as used herein refers to a region of an antibody, which comprises the CH2 and CH3 domains of the antibody heavy chain. Optionally, the Fc region may include a portion of the hinge region or the entire hinge region of the antibody heavy chain.

As used herein, "glucocorticoid-induced TNFR-related protein" or "GITR", also known as tumor necrosis factor receptor superfamily member 18 (TNFRSF18), means a GITR protein obtained or derived from any species, such as a mammalian species, especially a human. GITR includes both native GITR (i.e., full-length) and variations thereof (i.e., additions, deletions, insertions and/or substitutions of native GITR). One sequence for human GITR full-length (but without the signal peptide) is set forth in SEQ ID NO:20 (see also, UniProt/SwissProt Database Accession No. Q9Y5U5). One sequence for human GITR ECD (but without the signal peptide) is set forth in SEQ ID NO:21.

As used herein, "half-life" or "t½" means the time it takes for one-half of a quantity of a compound, such as a fusion protein described herein, to be removed from a fluid or other physiological space such as serum or plasma of an individual by biological processes. Alternatively, t½ also can mean a time it takes for a quantity of such a fusion protein to lose one-half of its pharmacological, physiological or radiological activity.

As used herein, "half-maximal effective concentration" or "$EC_{50}$" means a concentration of compound that results in 50% activation/stimulation of an assay endpoint, such as a dose-response curve.

As used herein, "in combination with" means administering at least one of the fusion proteins herein either simultaneously, sequentially or in a single combined formulation with one or more additional therapeutic agents.

As used herein, "individual in need thereof" means a mammal, such as a human, with a condition, disease, disorder or symptom requiring treatment or therapy, including for example, those listed herein. In particular, the preferred individual to be treated is a human.

As used herein, "long-acting" means that binding affinity and activity of a composition herein continues for a period of time greater than native peptide or protein, allowing for dosing at least as infrequently as once daily or even thrice-weekly, twice-weekly, once-weekly or monthly. The time action profile of the compounds herein may be measured using known pharmacokinetic test methods such as those described in the Examples below.

The terms "nucleic acid" or "polynucleotide", as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction.

As used herein, "non-standard amino acid" means an amino acid that may occur naturally in cells but does not participate in peptide synthesis. Non-standard amino acids can be constituents of a peptide and oftentimes are generated by modification of standard amino acids in the peptide (i.e., via post-translational modification). Non-standard amino acids can include D-amino acids, which have an opposite absolute chirality of the standard amino acids above.

As used herein, "oligomer" means a molecule having a few similar or identical repeating units that could be derived from copies of a smaller molecule, its monomer. These monomers can be joined by bonds that are either strong or weak, covalent or non-covalent (e.g., intramolecular).

As used herein, "patient," "subject" and "individual," are used interchangeably herein, and mean a mammal, especially a human. In certain instances, the individual is further characterized with a condition, disease, disorder or symptom that would benefit from administering a compound or composition herein.

As used herein, "pharmaceutically acceptable buffer" means any of the standard pharmaceutical buffers known to one of skill in the art.

As used herein, "sequence similarity" means a quantitative property of two or more nucleic acid sequences or amino acid sequences of biological compounds such as, for example, a correspondence over an entire length or a comparison window of the two or more sequences. Sequence similarity can be measured by (1) percent identity or (2) percent similarity. Percent identity measures a percentage of residues identical between two biological compounds divided by the length of the shortest sequence, whereas percent similarity measures identities and, in addition, includes sequence gaps and residue similarity in the evaluation. Methods of and algorithms for determining sequence similarity are well known in the art and thus need not be exhaustively described herein. A specified percentage of identical nucleotide or amino acid positions is at least about 75%, 80%, 85%, 86%, 87%, 88%, 89%, 90%, 91%, 92%, 93%, 94%, 95%, 96%, 97%, 98%, 99% or higher.

As used herein, "treating" or "to treat" means managing and caring for an individual having a condition, disease, disorder or symptom for which administration of a compound herein is indicated for the purpose of attenuating, restraining, reversing, slowing or stopping progression or severity of the condition, disease, disorder or symptom. Treating includes administering a compound herein or composition containing a compound herein to the individual to prevent the onset of symptoms or complications, alleviating the symptoms or complications, or eliminating the condition, disease, disorder or symptom. Treating includes administering a compound herein or composition containing a compound herein to the individual to result in such as, for example, decreased (or prevented) autoimmunity and/or reduced (or prevented) allergic disease, asthma, atopic dermatitis, joint inflammation, arthritis, rheumatoid arthritis, or other inflammatory disorders such as, IBD, CD and/or UC. The individual to be treated is a mammal, especially a human.

The term "therapeutically effective amount," as used herein, refers to an amount of a protein or nucleic acid or vector or composition that will elicit the biological or medical response of a subject, for example, reduction or inhibition of an enzyme or a protein activity, or ameliorate symptoms, alleviate conditions, slow or delay disease progression, or prevent a disease, etc. In a non-limiting embodiment, the term "a therapeutically effective amount" refers to the amount of a protein or nucleic acid or vector or composition that, when administered to a subject, is effective to at least partially alleviate, inhibit, prevent and/or ameliorate a condition, or a disorder or a disease.

As used herein, "variable heavy homodimer," "VHH" or "VHH moiety" means a form of single-domain antibody, especially an antibody fragment of a single, monomeric variable region of a heavy chain only antibody (HcAb), which has a very small size of about 15 kDa. It has been found herein that engineered/modified VHH-based compounds can be used as a pharmacokinetic enhancer to extend the duration of action of and/or to improve the t½ of biotherapeutics. The VHH-based compounds bind serum albumin; however, the VHH-based compounds can be used to bind IgG (including Fc domain), neonatal Fc receptor (FcRn) or other long-lasting serum proteins. The VHH-based compound therefore can be used to improve the t½ of a compound such as a peptide or protein or even other molecules such as, for example, small molecules.

Certain abbreviations are defined as follows: "ACR" refers to urine albumin/urine creatinine ratio; "AUC" refers to area under the curve; "$AUC_{0-inf}$" refers to area under the curve from time 0 hours to infinity; "cAMP" refers to cyclic adenosine monophosphate; "$C_0$" refers to estimated plasma concentration at time zero; "CL" refers to clearance following IV administration; "CL/F" refers to apparent clearance following SQ administration; "$C_{max}$" refers to maximum observed plasma concentration "CMV" refers to cytomegalovirus; "DNA" refers to deoxyribonucleic acid; "ECD" refers to extracellular domain; "EDC" refers to 1-ethyl-3-(3-dimethylaminopropyl) carbodiimide hydrochloride; "ETA" refers to ethanolamine; "GS" refers to glutamine synthetase; "HC" refers to heavy chain; "HIC" refers to hydrophobic interaction chromatography; "hr" refers to hour or hours; "IV" refers to intravenous; "kDa" refers to kilodaltons; "LC" refers to light chain; "LC-MS" refers to liquid chromatography-mass spectrometry; "min" refers to minute or minutes; "MS" refers to mass spectrometry; "MSX" refers to methionine sulfoximine; "NHS" refers to N-hydroxysuccinimide; "OtBu" refers to O-tert-butyl; "PEI" refers to polyethylenimine; "RP-HPLC" refers to reversed-phase high performance liquid chromatography; "sec" refers to second or seconds; "NaOAc" refers to sodium acetate; "rcf" means relative centrifugal force; "RT" means room temperature; "RU" means resonance units; "SQ" refers to subcutaneous; "SEC" refers to size-exclusion chromatography; "SEM" refers to standard error of the mean; "SPR" means surface plasmon resonance; "t½" refers to half-life; "TFA" refers to trifluoroacetic acid; "$T_{max}$" refers to time of maximum observed concentration; and "Trt" refers to trityl.

Anti-Human GITR Antigen Binding Fragment Compounds

The present disclosure provides an anti-human GITR antigen binding fragment compound comprising: 1) a heavy chain variable region (HCVR) comprising an HCDR1 having the amino acid sequence of SEQ ID NO: 1, an HCDR2 having the amino acid sequence of SEQ ID NO: 2 or 7, an HCDR3 having the amino acid sequence of SEQ ID NO: 3; and 2) a light chain variable region (LCVR) comprising an LCDR1 having the amino acid sequence of SEQ ID NO: 4, an LCDR2 having the amino acid sequence of SEQ ID NO: 5, and an LCDR3 having the amino acid sequence of SEQ ID NO: 6. In some instances, the anti-human GITR antigen binding fragment compound comprises a Fab comprising a human kappa CL and a human IgG1 CH1.

Compounds Having VHH-Based Half-Life Extenders

Briefly, certain compounds herein are of the formula (from N-terminus to C-terminus): X-L-M, wherein M is a compound acting as a t½-extending moiety, L (if present) is a linker, and X is an antibody Fab fragment that binds human GITR. In some instances, L can have an amino acid sequence comprising $(GGGGQ)_n$, $(GGGQ)_n$, $(GGGGS)_n$, $(PGPQ)_n$, $(PGPA)_n$, $GGGG(AP)_nGGGG$, $(GGE)_n$, (GGG- GE)$_n$, (GGK)$_n$, (GGGGK)$_n$, GGGG(EP)$_n$GGGG, GGGG (KP)$_n$GGGG, (PGPE)$_n$ or (PGPK)$_n$, where n can be from 1 to 15, especially from about 5 to about 10. In some instances, M is an albumin-binding VHH, and L is a peptide comprising an amino acid sequence of (GGGGQ)$_n$ where n can be from 1 to 15, especially from about 4 to about 8. In other instances, M comprises an amino acid sequence as shown in SEQ ID NO: 13, and L can have an amino acid sequence selected from SEQ ID NOS:11 or 12. In still other instances, L can have one or more additions, deletions, insertions or substitutions such that L has an amino acid sequence having at least about 90% to about 99% sequence similarity to any one of SEQ ID NOS:11 or 12. In still other instances, L can be a polymer such as a polyethylene glycol (PEG), especially (PEG)$_n$, where n can be from 1 to 20.

In some instances, the compounds disclosed herein are of the formula (from N-terminus to C-terminus): X-L-M, wherein M comprises an amino acid sequence as shown in SEQ ID NO:13 or having an amino acid sequence having at least about 90% to about 99% sequence similarity thereto, where L (if present) is a linker, and wherein X is a Fab that binds human GITR. In some instances, L can have an amino acid sequence comprising (GGGGQ)$_n$ where n can be from 1 to 15, especially from about 4 to about 8. In other instances, L can have an amino acid sequence selected from SEQ ID NOS:11 or 12. In still other instances, L can have one or more additions, deletions, insertions or substitutions such that L has an amino acid sequence having at least about 90% to about 99% sequence similarity to any one of SEQ ID NOS:11 or 12. In still other instances, L can be a polymer such as a polyethylene glycol (PEG), especially (PEG)$_n$, where n can be from 1 to 20. Preferably, the compound is a human GITR antagonist.

Pharmaceutical Compositions and Kits

In some instances, the anti-human GITR antigen binding fragment compounds disclosed herein such as the anti-human GITR Fabs, the anti-human GITR Fab fusions or conjugates to albumin-binding VHHs thereof (such as Antibody I and Antibody II disclosed herein) can be formulated as pharmaceutical compositions, which can be administered by parenteral routes (e.g., intravenous, intraperitoneal, intramuscular, subcutaneous or transdermal). Such pharmaceutical compositions and techniques for preparing the same are well known in the art. See, e.g., Remington, "The Science and Practice of Pharmacy" (D. B. Troy ed., 21$^{st}$ Ed., Lippincott, Williams & Wilkins, 2006). In particular instances, the compositions are administered SQ or IV. Alternatively, however, the compositions can be formulated in forms for other pharmaceutically acceptable routes such as, for example, tablets or other solids for oral administration; time release capsules, and any other form currently used, including creams, lotions, inhalants and the like.

As noted above, and to improve their in vivo compatibility and effectiveness, the VHH-based fusions or VHH-based conjugates herein may be reacted with any number of inorganic and organic acids/bases to form pharmaceutically acceptable acid/base addition salts. Pharmaceutically acceptable salts and common techniques for preparing them are well known in the art (See, e.g., Stahl et al., "Handbook of Pharmaceutical Salts: Properties, Selection and Use" (2$^{nd}$ Revised Ed. Wiley-VCH, 2011)). Pharmaceutically acceptable salts for use herein include sodium, trifluoroacetate, hydrochloride and acetate salts.

The compounds herein may be administered by a physician or self-administered using an injection. It is understood the gauge size and amount of injection volume can be readily determined by one of skill in the art. However, the amount of injection volume can be ≤about 2 mL or even ≤about 1 mL, and the needle gauge can be ≥about 27 G or even ≥about 29 G.

The disclosure also provides and therefore encompasses novel intermediates and methods useful for synthesizing the compounds herein, or a pharmaceutically acceptable salt thereof. The intermediates and compounds can be prepared by a variety of techniques that are well known in the art. For example, a method using recombinant synthesis is illustrated in the Examples below. The specific steps for each of the techniques described may be combined in different ways to prepare the compounds. The reagents and starting materials are readily available to one of skill in the art.

The compounds herein are generally effective over a wide dosage range. Exemplary doses of the compounds or of pharmaceutical compositions including the same can be milligram (mg) or microgram (μg) amounts per kilogram (kg) of an individual. In this manner, a daily dose can be from about 1 μg to about 1000 mg.

Here, the effective amount of the compound in a pharmaceutical composition can be a dose of about 2.5 mg to about 1000 mg. One of skill in the art, however, understands that in some instances the effective amount (i.e., dose/dosage) may be below the lower limit of the aforesaid range and be more than adequate, while in other cases the effective amount may be a larger dose and may be employed with acceptable side effects.

In addition to a compound herein, the pharmaceutical composition also can include at least one additional therapeutic agent such as, for example, a therapeutic agent typically used as the standard of care in of a particular condition, disease and disorder (e.g., a cardiovascular, neurological, immunological, metabolic, oncological, psychological, pulmonological and/or renal condition, disease or disorder).

In this manner, a pharmaceutical composition can include an effective amount of one or more compounds herein, a pharmaceutically acceptable carrier and optionally at least one additional therapeutic agent.

Alternatively, the compounds herein can be provided as part of a kit. In some instances, the kit includes a device for administering at least one compound (and optionally at least one additional therapeutic agent) to an individual. In certain instances, the kit includes a syringe and needle for administering the at least one compound (and optionally at least one additional therapeutic agent). In particular instances, the compound (and optionally at least one additional therapeutic agent) is pre-formulated in aqueous solution within the syringe.

Methods of Making and Using VHH-Based Compounds Acting as Half-Life Extenders or Fusions and Conjugates Thereof The compounds herein can be made via any number of standard recombinant DNA methods or standard chemical peptide synthesis methods known in the art. With regard to recombinant DNA methods, one can use standard recombinant techniques to construct a polynucleotide having a nucleic acid sequence that encodes an amino acid sequence for a compound (i.e., fusion peptide or fusion protein or fusion conjugate), incorporate that polynucleotide into recombinant expression vectors, and introduce the vectors into host cells, such as bacteria, yeast and mammalian cells, to produce the compound. (See, e.g., Green & Sambrook, "Molecular Cloning: A Laboratory Manual" (Cold Spring Harbor Laboratory Press, 4$^{th}$ ed. 2012)).

With regard to recombinant DNA methods, the compounds herein can be prepared by producing a protein or precursor protein molecule using recombinant DNA techniques. DNA, including cDNA and synthetic DNA, may be double-stranded or single-stranded, and the coding sequences therein encoding a compound herein may vary as a result of the redundancy or degeneracy of the genetic code. Briefly, the DNA sequences encoding the compounds herein are introduced into a host cell to produce the compound or precursor thereof. The host cells can be bacterial cells such as K12 or B strains of *Escherichia coli*, fungal cells such as yeast cells, or mammalian cells such as Chinese hamster ovary (CHO) cells.

An appropriate host cell is transiently or stably transfected or transformed with an expression system, such as expression vectors, for producing a compound herein or a precursor thereof. Expression vectors typically are replicable in the host organisms either as episomes or as an integral part of the host chromosomal DNA. Commonly, expression vectors will contain selection markers such as, for example, tetracycline, neomycin, G418 and dihydrofolate reductase, to permit selection of those cells transformed with the desired DNA sequences.

The specific biosynthetic or synthetic steps for each of the steps described herein may be used, not used or combined in different ways to prepare the compounds herein.

With regard to chemical peptide synthesis methods, one can use standard manual or automated solid-phase synthesis procedures. For example, automated peptide synthesizers are commercially available from, for example, Applied Biosystems (Foster City, CA) and Protein Technologies Inc. (Tucson, AZ). Reagents for solid-phase synthesis are readily available from commercial sources. Solid-phase synthesizers can be used according to the manufacturer's instructions for blocking interfering groups, protecting amino acids during reaction, coupling, deprotecting and capping of unreacted amino acids.

The methods can include the steps described herein, and these maybe be, but not necessarily, carried out in the sequence as described. Other sequences, however, also are conceivable. Moreover, individual or multiple steps may be carried out either in parallel and/or overlapping in time and/or individually or in multiply repeated steps. Furthermore, the methods may include additional, unspecified steps.

Such methods therefore can include selecting an individual having, for example, a autoimmune condition, disease or disorder, or who is predisposed to the same.

The methods also can include administering to the individual an effective amount of at least one compound herein, which may be in the form of a pharmaceutical composition as also described herein. In some instances, the compound/pharmaceutical composition can include an additional therapeutic agent.

The concentration/dose/dosage of the compound and optional additional therapeutic agent are discussed elsewhere herein.

With regard to a route of administration, the compound or pharmaceutical composition including the same can be administered in accord with known methods such as, for example, orally; by injection (i.e., intra-arterially, intravenously, intraperitoneally, intracerebrally, intracerebroventricularly, intramuscularly, intraocularly, intraportally or intralesionally); by sustained release systems, or by implantation devices. In certain instances, the compound or pharmaceutical composition including the same can be administered SQ by bolus injection or continuously.

With regard to a dosing frequency, the compound or pharmaceutical composition including the same can be administered daily, every other day, three times a week, two times a week, one time a week (i.e., weekly), biweekly (i.e., every other week), or monthly. In certain instances, the compound or pharmaceutical composition including the same is administered SQ every other day, SQ three times a week, SQ two times a week, SQ one time a week, SQ every other week or SQ monthly. In particular instances, the compound or pharmaceutical composition including the same is administered SQ one time a week (QW).

Alternatively, and if administered IV, the compound or pharmaceutical composition including the same is administered IV every other day, IV three times a week, IV two times a week, IV one time a week, IV every other week or IV monthly. In particular instances, the compound or pharmaceutical composition including the same is administered IV one time a week (IW).

With regard to those instances in which the compound or pharmaceutical composition including the same is administered in combination with an effective amount of at least one additional therapeutic agent, the additional therapeutic agent can be administered simultaneously, separately or sequentially with the compound or pharmaceutical composition including the same.

Moreover, the additional therapeutic agent can be administered with a frequency same as the compound or pharmaceutical composition including the same (i.e., every other day, twice a week, or even weekly). Alternatively, the additional therapeutic agent can be administered with a frequency distinct from the compound or pharmaceutical composition including the same. In other instances, the additional therapeutic agent can be administered SQ. In other instances, the additional therapeutic agent can be administered IV. In still other instances, the additional therapeutic agent can be administered orally.

It is further contemplated that the methods may be combined with additional therapeutic agents other than those discussed above.

EXAMPLES

The following non-limiting examples are offered for purposes of illustration, not limitation.

Polypeptide Expression

Example 1: Recombinant Expression of Antibody I

Antibody I is an anti-human GITR Fab—albumin-binding VHH fusion having a heavy chain amino acid sequence of:

```
                                                (SEQ ID NO: 14)
QVQLVESGGGVVQPGRSLRLSCAASGYTFSSYVMHWVRQAPGKGLEWVAV

TSYDGTHEYYADSVKGRFTISRDNSKNTLYLQMNSLRAEDTAVYYCAREN

NWAPDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTGGGGQGGGGQGGGGQGGGGQGGGGQ

EVQLLESGGGLVQPGGSLRLSCAASGRYIDETAVAWFRQAPGKGREFVAG

IGGGVDITYYADSVKGRFTISRDNSKNTLYLQMNSLRPEDTAVYYCAARP

GRPLITSKVADLYPYWGQGTLVTVSSPP;
``` and a light chain amino acid sequence of:

```
                                              (SEQ ID NO: 16)
DIQMTQSPSSLSASVGDRVTITCRASQDISNSLAWYQQKPGKAPKRLIYA

AIFSLQSGVPSRFSGSGSGTEFTLTISSLQPEDFATYYCYQYYNYPSAFG

QGTKLEIKRTVAAPSVFIFPPSDFQLKSGTASVVCLLNNFYPREAKVQWI

KVDNALQSGNSQESVTEQDSKDSTYSLSSTLTLSKADYEKHKVYACEVTH

QGLSSPVTKSFNRGEC.
```

The antibody with the heavy chain of SEQ ID NO:14 and the light chain of SEQ ID NO:16 is generated in a mammalian cell expression system using CHOK1 cell derivatives (Lonza Biologics Inc.). The cDNA sequences encoding SEQ ID NO:14 and SEQ ID NO:16 are sub-cloned into GS-containing expression plasmid backbones (pEE12.4-based plasmids; Lonza Biologics Inc.). The cDNA sequence is fused in frame with the coding sequence of a signal peptide sequence, METDTLLLWVLLLWVPGSTG (SEQ ID NO:22), to enhance secretion of the antibody into the tissue culture medium. The expression is driven by the viral CMV promoter.

For generating the antibody via transient transfection, CHOK1 cells are transfected with an equal stoichiometric ratio of the recombinant expression plasmids using a PEI-based method. Briefly, the appropriate volume of CHOK1 suspension cells at a density of $4 \times 10^6$ cells/mL is transferred in shake flasks, and both PEI and recombinant plasmid DNA are added to the cells. Cells are incubated in a suspension culture at 32° C. for 6 days. At the end of the incubation period, cells are removed by low-speed centrifugation and the antibody is purified from the conditioned medium.

Alternatively, and for generating the antibody via stable transfections, CHOK1 cells are stably transfected using electroporation and the appropriate amount of recombinant expression plasmid, and the transfected cells are maintained in suspension culture at an adequate cell density. Selection of the transfected cells is accomplished by growth in 25 µM MSX-containing serum-free medium and incubated at about 35° C.-37° C. and about 5%-7% $CO_2$. Subsequently, cells are removed by low-speed centrifugation and the antibody is purified from the conditioned medium.

The antibody is secreted into the media from the CHO cells, which is purified by Protein A affinity chromatography followed by cation exchange chromatography. Specifically, the antibody from harvested media is captured onto Mab-Select PrismA Protein A resin (Cytiva). The resin then is briefly washed with a wash buffer, such as a phosphate-buffered saline (PBS; pH 7.4) or a buffer containing Tris, to remove non-specifically bound material. The protein is eluted from the resin with a low pH solution, such as 10 mM citric acid pH 3. Fractions containing the antibody are pooled and may be held at a low pH to inactivate potential viruses. The pH may be neutralized by adding a base such as 0.1 M Tris pH 8.0. The antibody may be further purified by ion exchange chromatography using resins such as POROS 50 HS (ThermoFisher). The antibody may be eluted from the column using a 0 to 1M NaCl gradient in 20 mM sodium acetate, pH 5.0 over 20 column volumes.

Purified antibody may be buffer exchanged into phosphate buffered saline or, alternatively, passed through a viral retention filter such as Planova 20N (Asahi Kasei Medical) followed by concentration/diafiltration into phosphate buffered saline using tangential flow ultrafiltration on a regenerated cellulose membrane (Millipore).

The antibody therefore is prepared in this manner or in a similar manner that would be readily determined by one of skill in the art.

TABLE 1

SEQ ID NOs for Antibody I
Antibody I

| Amino Acid Sequence for: | SEQ ID NO: |
|---|---|
| HCDR1 | 1 |
| HCDR2 | 2 |
| HCDR3 | 3 |
| LCDR1 | 4 |
| LCDR2 | 5 |
| LCDR3 | 6 |
| HCVR | 8 |
| LCVR | 10 |
| Linker | 11 |
| Albumin-binding VHH | 13 |
| HC anti-GITR Fab-VHH Fusion | 14 |
| LC | 16 |
| DNA Sequence for: | |
| HC anti-GITR Fab-VHH Fusion | 17 |
| LC | 19 |

Example 2: Recombinant Expression of Antibody II

Antibody II is an anti-human GITR Fab—albumin-binding VHH fusion having a heavy chain amino acid sequence of:

```
                                              (SEQ ID NO: 15)
QVQLVESGGGVVQPGRSLRLSCAASGYTFSSYVMHWVRQAPGKGLEWVAV

TSYDGTHELYADSVKGRFTISRDNSKNTLYLQMNSLRAEDTAVYYCAREN

NWAPDYWGQGTLVTVSSASTKGPSVFPLAPSSKSTSGGTAATGCLVKDYF

PEPVTVSWNSGALTSGVHTFPAVLQSSGLYSLSSVVTVPSSSLGTQTYIC

NVNHKPSNTKVDKKVEPKSCDKTHTGGGGQGGGGQGGGGQGGGGQGGGGQ

EVQLLESGGGLVQPGGSLRLSCAASGRYIDETAVAWFRQAPGKGREFVAG

IGGGVDITYYADSVKGRFTISRDNSKNTLYIQMNSLRPEDTAVYNCAARP

GRPLTSKVADLYPYWGQGTLVTVSSPP
``` and a light chain amino acid sequence of:

```
                                              (SEQ ID NO: 16)
DIQMTQSPSSLSASVGDRVTITCRASQDISNSLAWYQQKPGKAPKRLIYA

AFSLQSGVPSRFSGSGSGTEFTLTISSLQPEDFATYYCYQYYNYPSAFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

The antibody with the heavy chain of SEQ ID NO:15 and the light chain of SEQ ID NO:16 is generated essentially as described for Example 1 except that cDNA sequences encoding SEQ ID NOs:15 and 16 are used in the expression plasmids.

TABLE 2

SEQ ID NOs for Antibody II
Antibody II

| | SEQ ID NO: |
|---|---|
| Amino Acid Sequence for: | |
| HCDR1 | 1 |
| HCDR2 | 7 |
| HCDR3 | 3 |
| LCDR1 | 4 |
| LCDR2 | 5 |
| LCDR3 | 6 |
| HCVR | 9 |
| LCVR | 10 |
| Linker | 11 |
| Albumin-binding VHH | 13 |
| HC anti-GITR Fab-VHH Fusion | 15 |
| LC | 16 |
| DNA Sequence for: | |
| HC anti-GITR Fab-VHH Fusion | 18 |
| LC | 19 |

Example 3: Antibody Binding to Albumin Orthologs by SPR

In vitro binding of the antibodies (i.e., anti-human GITR Fab—albumin-binding VHH fusions) to human, cynomolgus monkey, mouse, rat, pig, dog, cow and rabbit serum albumin is determined by SPR at 25° C. In particular, the affinity of Antibodies I and II to serum albumin of these species is summarized below in Tables 3 and 4, respectively.

Binding of Antibody I and Antibody II to various serum albumins is carried out on Biacore 8K instrument. The immobilization of the serum albumin to a Series S Sensor Chip CM5 (Cytiva 29149603) surface is performed according to the manufacturer's instructions (Amine Coupling Kit BR-1000-50). Briefly, carboxyl groups on the sensor chip surfaces (flow cell 1 and 2) are activated by injecting 70 μL of a mixture containing 75 mg/ml 1-Ethyl-3-(3-dimethyl-aminopropyl) carbodiimide hydrochloride (EDC), and 11.5 mg/ml N-Hydroxysuccinimide (NHS) at 10 μl/min. Human, cynomolgus monkey, rat, mouse, dog, pig, cow, and rabbit serum albumin are diluted in 10 mM sodium acetate pH 4.0 (BR-1003-49) at 0.8, 0.8, 0.8, 2.5, 0.8, 1, 1, and 1.5 μg/ml then injected over the activated chip surfaces (flow cell 2, channel 1 to 8) at 10 μl/min for 100 seconds. Human serum albumin was obtained from Sigma Aldrich (St. Louis, MO) (Cat. No. A8763). Cynomolgus monkey serum albumin was obtained from Athens R&T (Athens, GA) (Cat. No. 16-16-011202-CM). Rat serum albumin was obtained from Sigma Aldrich (St. Louis, MO) (Cat. No. A4538). Mouse serum albumin was obtained from Sigma Aldrich (St. Louis, MO) (Cat. No. A3139). Dog serum albumin was obtained from Molecular Innovations (Novi, MI) (Cat. No. DSA-1213 NC0739153). Pig serum albumin was obtained from Sigma Aldrich (St. Louis, MO) (Cat. No. A4414). Cow serum albumin was obtained from Sigma Aldrich (St. Louis, MO) (Cat. No. A7030). Rabbit serum albumin was obtained from Fitzgerald Industries International (Acton, MA) (Cat. No. 30R-3303).

The serum albumins are covalently immobilized through free amines onto a carboxymethyl dextran-coated sensor chip CM5 at surface densities of 29-52 resonance units (RU) for human, cynomolgus monkey, rat, mouse, dog, pig, and cow as well as 118 resonance units (RU) for rabbit serum albumin. Excess reactive groups on the surfaces (flow cell 1 and 2) are deactivated by injecting 70 μl of 1 M Ethanolamine hydrochloride-NaOH pH 8.5.

The antibodies of Examples 1 and 2 (i.e., Antibody I and II, respectively) are diluted in HBS-EP+buffer (10 mM HEPES pH 7.6, 150 mM NaCl, 3 mM EDTA, 0.05% Polysorbate 20) at concentrations of 1000, 333.3, 111.1, 37.04, 12.35, 4.12, 1.37, 0.457, 0.152, 0.051 and 0.017 nM. 180 μl of sample are individually injected sequentially across the immobilized serum albumins on the chip's surface and dissociated for 600 sec at 60 μl/min flow rate at 25° C. The surface is regenerated by injecting 10 mM glycine-HCl pH 1.5 (BR-1003-54) at 60 μl/min for 100 sec. The resulting sensorgrams are analyzed using Biacore 8K Insight Evaluation Software (version 3.0.11.15423) 1:1 binding kinetics model fitting to calculate the binding kinetic parameters: association rate (ka), dissociation rate (kd), and equilibrium dissociation constant ($K_D$). $K_D$ is determined as 0.25, 4.4, 53, 44, 100, 20, and 460 nM for human, cynomolgus monkey, mouse, rat, pig, dog and cow serum albumin binding, respectively, with Antibody I (Table 3). KD is determined as 0.4, 5.9, 42, 51, 99, 20 and 430 nM for human, cynomolgus monkey, mouse, rat, pig, dog and cow serum albumin binding, respectively, with Antibody II (Table 4).

TABLE 3

Binding Kinetics of Antibody I to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 2.6E+05 | 6.5E−05 | 2.5E−10 |
| Cyno SA | 1.9E+05 | 8.2E−04 | 4.4E−09 |
| Mouse SA | 1.8E+05 | 9.4E−03 | 5.3E−08 |
| Rat SA | 1.6E+05 | 7.0E−03 | 4.4E−08 |
| Pig SA | 1.2E+05 | 1.3E−02 | 1.0E−07 |
| Dog SA | 1.7E+05 | 3.5E−03 | 2.0E−08 |
| Cow SA | 2.0E+05 | 9.1E−02 | 4.6E−07 |
| Rabbit SA | | No binding | |

TABLE 4

Binding Kinetics of Antibody II to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.9E+05 | 7.8E−05 | 4.0E−10 |
| Cyno SA | 1.5E+05 | 8.7E−04 | 5.9E−09 |
| Mouse SA | 2.3E+05 | 9.6E−03 | 4.2E−08 |
| Rat SA | 1.4E+05 | 7.3E−03 | 5.1E−08 |
| Pig SA | 1.2E+05 | 1.2E−02 | 9.9E−08 |
| Dog SA | 1.7E+05 | 3.4E−03 | 2.0E−08 |
| Cow SA | 2.0E+05 | 8.7E−02 | 4.3E−07 |
| Rabbit SA | | No binding | |

Example 4: Antibody Binding to GITR Expressing Cells

Jurkat human GITR/NFkB-Luc2 cells (CS184004) were purchased from Promega and maintained in RPMI1640 media+10% FBS (HyClone SH30070.3)+400 μg/mL hygromycin B+600 μg/mL G418.

The NFkB reporter pNiFty2-Luc (InvivoGen) is introduced into Jurkat cells (ATCC) by electroporation and transfectants are selected with 400 μg/mL zeocin for 2 weeks. The resulting Jurkat NFkBluc cell line is transduced with cynomolgus monkey GITR lentivirus and selected with 0.5 µg/mL puromycin for 1 week. Jurkat cyno GITR/NFkBluc cells are maintained in RPMI1640 media+10% FBS (HyClone SH30070.3)+400 µg/mL zeocin+0.5 µg/mL puromycin.

Jurkat human GITR/NFkB-Luc2 and Jurkat cynomolgus monkey GITR/NFkBluc cells are resuspended in FACS buffer (PBS+1% BSA+0.01% sodium azide) at 1 million cells/mL and 5 µl Fc block/mL (BioLegend) is added and incubated at 4° C. for 20 min. Cells are washed with FACS buffer and resuspended at 1e6 cells/mL in FACS buffer and added to a polypropylene 96-well plate at 100 µl/well for 100,000 cells/well. 100 µl/well of 2X antibody dose titrations diluted in FACS buffer are added to cells and incubated 45 minutes at 4° C. Cells are washed twice with 200 µl/well FACS buffer and resuspended in 12.5 µg/mL anti-human Ig light chain kappa/PE secondary antibody (Invitrogen #PA1-74408) in FACS buffer and incubated for 45 minutes at 4° C. Cells are washed twice with 200 µl/well FACS buffer and resuspended in 200 µl FACS buffer. Samples are read on a Millipore EasyCyte Cytometer and median fluorescence intensity values are calculated using GuavaSoft 3.3 InCyte software. $EC_{50}$ values are calculated for each of 3 experiment replicates and the $EC_{50}$ Geometric Mean +/−Error (Delta Method) is calculated from these 3 results. The cell binding results shown in Table 5 indicate that both Antibody I and Antibody II bind potently to human GITR and cynomolgus monkey GITR ("cyno GITR"). On the other hand, an adalimumab Fab-albVHH used as a negative control for this study demonstrated negligible binding to human GITR and cynomolgus monkey GITR (data not shown).

TABLE 5

In Vitro Potency of Antibodies Binding to Jurkat GITR cell lines.

| Compound | Human GITR cell binding $EC_{50}$ nM GeoMean | Error (delta method) | N | Cyno GITR cell binding $EC_{50}$ nM GeoMean | Error (delta method) | N |
|---|---|---|---|---|---|---|
| Antibody I | 6.80 | 0.30 | 3 | 3.06 | 0.04 | 3 |
| Antibody II | 3.25 | 0.12 | 3 | 2.34 | 0.06 | 3 |

Example 5: Antibody In Vitro GITRL Antagonism at Human and Cyno GITR

Jurkat human GITR/NFkB-Luc2 or Jurkat cyno GITR/NFkBluc cells are starved overnight in assay media (RPMI1640+1% FBS) at 37° C., 5% $CO_2$ and resuspended the next day in assay media (RPMI1640+1% FBS) at 2e6 cells/mL. 25 µL/well of cell suspension is added to white opaque 96-well plates (Corning Costar) for 5e5 cells/well. 50 µL/well of 2X antibody dose titrations diluted in assay media are added, immediately followed by addition of 25 µL/well of 4X (12 nM) human GITRL or cyno GITRL, respectively, diluted in assay media. Plates are incubated at 37° C., 5% $CO_2$ for 6 hours and then placed at room temperature for 15 minutes. 100 µL/well of BioGlo luciferase reagent (Promega) is added per well and incubated with shaking for 5 minutes at room temperature. Luminescence is measured with a BioTek SynergyNeo2 plate reader with Gen5 software. $IC_{50}$ values are calculated for GITRL inhibition by GITR antagonist antibody treatments from each of 3 experiment replicates and the $IC_{50}$ Geometric Mean with Error (delta method) is calculated from these 3 results.

TABLE 6

In Vitro Potency of GITR Antagonist Antibodies for Inhibition of GITRL Stimulation of Jurkat GITR/NFkB luciferase Cells.

| Compound | Human GITR $IC_{50}$ nM GeoMean | Error (delta method) | N | Cyno GITR $IC_{50}$ nM GeoMean | Error (delta method) | N |
|---|---|---|---|---|---|---|
| Antibody I | 4.10 | 0.98 | 3 | 2.27 | 0.37 | 3 |
| Antibody II | 1.68 | 0.18 | 3 | 1.26 | 0.09 | 3 |

The luciferase reporter functional bioassay results in Table 6 demonstrate that both Antibody I and Antibody II potently inhibit human GITRL stimulation of human GITR and cyno GITRL stimulation of cyno GITR.

Example 6: Antibody In Vitro Agonism at Human and Cyno GITR

Jurkat human GITR/NFkB-Luc2 or Jurkat cyno GITR/NFkBluc cells are starved overnight in assay media (RPMI1640+1% FBS) at 37° C., 5% $CO_2$ and resuspended the next day in assay media (RPMI1640+1% FBS) at 2e6 cells/mL. 50 µL/well of cell suspension is added to white opaque 96-well plates (Corning Costar) for 5e5 cells/well. 50 µL/well of 2X antibody dose titrations diluted in assay media are added and plates are incubated at 37° C., 5% $CO_2$ for 6 hours and then placed at room temperature for 15 minutes. 100 µL/well of BioGlo luciferase reagent (Promega) is added per well and incubated with shaking for 5 minutes at room temperature. Luminescence is measured with a BioTek SynergyNeo2 plate reader with Gen5 software. $EC_{50}$ values are calculated for GITR antibody treatments from each of 2 or 3 experiment replicates and the $EC_{50}$ Geometric Error (delta method) is calculated from these results.

TABLE 7

In Vitro GITR Antibody Agonism of Jurkat GITR/NFkB luciferase Cells.

| Compound | Human GITR $EC_{50}$ nM GeoMean | N | Cyno GITR $IC_{50}$ nM GeoMean | N |
|---|---|---|---|---|
| Antibody I | no activity | 3 | no activity | 3 |
| Antibody II | no activity | 3 | no activity | 3 |
| Antibody III | 8.50 | 2 | 0.52 | 2 |

The luciferase reporter functional bioassay results in Table 7 demonstrate that treatment of Jurkat human GITR/NFkB luciferase or Jurkat cyno GITR/NFkB luciferase cells with Antibody I or Antibody II in the absence of GITRL did not result in agonist stimulation. In contrast, treatment with a bivalent IgG variant of Antibody I (i.e., Antibody III) did induce GITR pathway activation.

Example 7: Antibody In Vitro Antagonism of GITRL Co-Stimulation of T cell Proliferation One aspect of GITRL biology is its ability to co-stimulate T cells, resulting in increased proliferation. In this example, it is demonstrated that Antibody I and Antibody II treatment potently inhibits plate-bound GITRL co-stimulation of human T cell proliferation. Human CD3+ T cells were isolated from peripheral blood mononuclear cells (PBMCs) and stimulated at 1.5e6 cells/mL with plate-bound 0.2 µg/mL anti-CD3 antibody for 4 days to increase GITR expression on T cells. T cells were then rested in culture medium for 2 days to prepare cells for restimulation. Activated and rested T cells at 1.5e6 cells/mL were then co-stimulated with plate-bound 2 μg/mL anti-CD3 antibody and 1 nM human GITRL for 5 days in the presence of Antibody I or Antibody II dose titrations. T cell proliferation was measured by H3-thymidine uptake during the last 18 hours of incubation. Each antibody was tested with triplicate dose titration conditions and tested on four different donors over three separate experiments.

TABLE 8

In Vitro Potency of GITR Antagonist Antibodies for Inhibition of GITRL co-stimulation of T cell proliferation.

| Compound | Human GITR $IC_{50}$ nM GeoMean | Error (delta method) | N |
|---|---|---|---|
| Antibody I | 4.76 | 1.42 | 4 |
| Antibody II | 1.84 | 0.52 | 4 |

The GITRL co-stimulation assay results shown in Table 8 demonstrate that Antibody I and Antibody II potently inhibit GITRL co-stimulation of T cell proliferation. In contrast, an albVHH antibody fragment used as a negative control demonstrated negligible ability to inhibit GITRL co-stimulation of T cell proliferation (data not shown).

Example 8: Antibody Restoration of In Vitro Regulatory T Cell Suppression of Effector T Cell Proliferation in the Presence of GITRL One aspect of GITRL biology is its ability to inhibit regulatory T cell suppression of effector T cell proliferation through binding and activation of GITR. In this example, we demonstrate that Antibody I and Antibody II treatment potently restores the suppressive activity of regulatory T cells in the presence of plate-bound GITRL. Human T cells and CD4+CD127lowCD25+ regulatory T cells were isolated from peripheral blood mononuclear cells (PBMCs) and were labeled with CellTrace CFSE or CellTrace Violet (Invitrogen), respectively. T cells and CD4+CD127lowCD25+ regulatory T cells were combined at a 2:1 ratio in the presence of Antibody I or Antibody II dose titrations and stimulated with 2 μg/mL anti-CD28 and plate-bound 1 μg/mL anti-CD3 and 2 nM GITRL. After incubation for four days, proliferation of CD4+ T cells was evaluated by flow cytometry tracking CFSE labeling, excluding CellTrace Violet labeled CD4+CD127lowCD25+ regulatory T cells. The assay was performed with four individual donors on four separate occasions. 10,000 events were acquired per treatment (single biological replicate per antibody concentration tested) and used to calculate the percent proliferation of T effector cells.

TABLE 9

In Vitro Potency of GITR Antagonist Antibodies for Restoration of Regulatory T cell Suppression of Effector T cell Proliferation in the presence of GITRL

| Compound | Human GITR $IC_{50}$ nM Mean | Error (delta method) | N |
|---|---|---|---|
| Antibody I | 4.69 | 0.20 | 4 |
| Antibody II | 2.72 | 0.83 | 4 |

The assay results shown in Table 9 demonstrate that Antibody I and Antibody II potently restore regulatory T cell suppression of effector T cell proliferation in the presence of GITRL.

Example 9: Antibody Pharmacokinetics in Mice

Male C57BL/6 mice are administered a single IV or SQ dose of 10 mg/kg of Antibody I or Antibody II in PBS (pH 7.4) at a volume of 0.1 mL/animal. For pharmacokinetic characterization, blood is collected from 3 animals/group/timepoint at 1, 6, 24, 48, 72, 96, 120, 168, 240, and 336 hours post IV dose or at 3, 6, 12, 24, 48, 96, 120, 168, 240, and 336 hours post SQ dose and processed to plasma.

Plasma concentrations of Antibodies I and II are determined by a plate-based GITR antigen capture enzyme-linked immunosorbent assay (ELISA) method. A recombinant human GITR Fc chimera (rh GITR/TNFRSF18 Fc) is coated on the ELISA plate as a capture reagent at 1 mg/mL. After incubation with plasma standards, control and samples, a goat anti-human Ig Fab horseradish peroxidase is used to detect plate-bound Antibody I or Antibody II. Pharmacokinetic parameters are calculated using non-compartmental analysis (NCA) of mean concentrations determined at each time point (N=1 to 3 animals/group/time point). NCA is performed using Watson Bioanalytical LIMS. As shown in Table 10, Antibodies I and II demonstrate an extended pharmacokinetic profile in C57BL/6 mice.

TABLE 10

Composite Plasma Pharmacokinetic Parameters for Antibodies I and II Following a Single 10 mg/kg IV or SQ Dose to Male C57BL/5 Mice.

| Antibody | Route | $C_0$ (μg/mL) | $C_{max}$ (μg/mL) | $T_{max}$ (hr) | $AUC_{0-inf}$ (hr*μg/mL) | CL or CL/F (mL/hr/kg) | $t_{1/2}$ (hr) | % F |
|---|---|---|---|---|---|---|---|---|
| I | IV | 86.8 | NA | NA | 5630 | 1.78 | 50.6 | NA |
| I | SQ | NA | 42.4 | 12 | 3270 | 3.06 | 40.7 | 58.1 |
| II | IV | 124 | NA | NA | 5430 | 1.84 | 29.3 | NA |
| II | SQ | NA | 69.2 | 12 | 3500 | 2.86 | 34.6 | 64.5 |

Example 10: Antibody Pharmacokinetics in Rats

Male Sprague Dawley rats are administered a single IV or SQ dose of 10 mg/kg Antibody I or Antibody II in PBS (pH 7.4) at volumes of 2.5 mL/kg and 1 mL/kg, respectively. For pharmacokinetic characterization, blood is collected from 3 animals/group/timepoint at 1, 6, 24, 48, 72, 96, 120, 168, 240, 336, 432 and 504 hours post IV dose or at 3, 6, 12, 24, 48, 96, 120, 168, 240, 336, 432 and 504 hours post SQ dose and processed to plasma.

Plasma concentrations of Antibody Antibodies I and II are determined by a plate-based GITR antigen capture enzyme-linked immunosorbent assay (ELISA) method. A recombinant human GITR Fc chimera (rh GITR/TNFRSF18 Fc) was coated on the ELISA plate as a capture reagent at 1 μg/mL. After incubation with plasma standards, control and samples, a goat anti-human Ig Fab horseradish peroxidase (diluted 1:10,000) was used to detect plate-bound Antibody I or Antibody II. Pharmacokinetic parameters are calculated using NCA for each animal (N=2-3) and parameters are summarized by the mean and standard deviation (SD), where appropriate. Pharmacokinetic data were available for N=2 rats dosed subcutaneously with Antibody II and therefore mean parameters are reported. NCA and summary statistic calculations are performed using Watson Bioanalytical LIMS. As shown in Table 11 and Table 12, Antibody Antibodies I and II has demonstrate an extended pharmacokinetic profile in Sprague Dawley rats.

TABLE 11

Plasma Pharmacokinetic Parameters for Antibody I Following a Single 10 mg/kg IV (N = 3) or 10 mg/kg SQ (N = 3) Dose to Male Sprague Dawley Rats.

| Antibody | Route | $C_0$ (µg/mL) | $C_{max}$ (µg/mL) | $T_{max}$ (hr) | $AUC_{0-inf}$ (hr*µg/mL) | CL or CL/F (mL/hr/kg) | $t_{1/2}$ (hr) | % F |
|---|---|---|---|---|---|---|---|---|
| I | IV | 289 (24.3) | NA | NA | 14600 (1710) | 0.69 (0.08) | 54.0 (1.36) | NA |
| I | SQ | NA | 48.8 (6.87) | 48 (0) | 6630 (267) | 1.51 (0.06) | 55.4 (1.99) | 45.4 |

NOTE:
Parameters are reported as mean (SD).

TABLE 12

Plasma Pharmacokinetic Parameters for Antibody II Following a Single 10 mg/kg IV (N = 3) or 10 mg/kg SQ (N = 2) Dose to Male Sprague Dawley Rats.

| Antibody | Route | $C_0$ (µg/mL) | $C_{max}$ (µg/mL) | $T_{max}$ (hr) | $AUC_{0-inf}$ (hr*µg/mL) | CL or CL/F (mL/hr/kg) | $t_{1/2}$ (hr) | % F |
|---|---|---|---|---|---|---|---|---|
| II | IV | 188 (19.4) | NA | NA | 10900 (473) | 0.92 (0.04) | 53.0 (6.90) | NA |
| II | SQ | NA | 24.2 | 48 | 3540 | 2.86 | 55.6 | 32.5 |

NOTE:
Parameters are reported as mean (SQ route) or mean (SD) (IV route).

Example 11: Antibody Pharmacokinetics in Cynomolgus Monkey

Cynomolgus monkeys are administered a single 0.1, 1, or 10 mg/kg IV dose or 10 mg/kg SQ dose of Antibody I or Antibody II in PBS (pH 7.2) at volumes of 1 mL/kg (IV) or 0.2 mL/kg (SC). For pharmacokinetic characterization, blood is collected from 3 animals/group/timepoint at 0.5, 3, 6, 24, 48, 72, 96, 168, 240, 336, 432, 504 and 672 hours post dose and processed to plasma.

Plasma concentrations of Antibodies I and II are determined by plate-based GITR antigen capture enzyme-linked immunosorbent assay (ELISA) methods. A recombinant human GITR Fc chimera (rh GITR/TNFRSF18 Fc) is coated on the ELISA plate as a capture reagent at 1 µg/mL. After incubation with plasma standards, control and samples, detections antibodies are used to determine the stability of the antibodies. In one method, a goat anti-human Ig Fab horseradish peroxidase is used to detect the Fab-portion of plate-bound Antibody I or Antibody II. In the second method, a Biotin-SP AffiniPure Goat Anti-Alpaca IgG, VHH domain is added as a secondary antibody to detect metabolically stable antibody with intact linker of plate-bound Antibody I or Antibody II. Following this incubation, a peroxidase-conjugated streptavidin is added as a reagent to detect plate-bound Antibody I or Antibody II. Pharmacokinetic parameters are calculated using NCA for each animal and parameters are summarized by the mean and standard deviation (SD), where appropriate. NCA and summary statistic calculations are performed using Watson Bioanalytical LIMS. As shown in Table 13 and Table 14, Antibodies I and II demonstrate an extended pharmacokinetic profile in cynomolgus monkeys. When comparing concentrations of Antibodies I or II measured with both ELISA methods, similar exposure and pharmacokinetics was observed, indicating metabolic stability of these antibodies in vivo following IV or SQ administration.

TABLE 13

Plasma Pharmacokinetic Parameters for Antibody I Following a Single 0.1 (N = 1), 1 (N = 2), or 10 mg/kg IV (N = 2) or 10 mg/kg SQ (N = 2) Dose to Cyno Monkeys.

| ELISA Method | Route | Dose (mg/kg) | $C_0$ (µg/mL) | $C_{max}$ (µg/mL) | $T_{max}$ (hr) | $AUC_{0-inf}$ (hr*µg/mL) | CL or CL/F (mL/hr/kg) | $t_{1/2}$ (hr) | % F |
|---|---|---|---|---|---|---|---|---|---|
| anti-Fab detection | IV | 0.1 | 2.25 | NA | NA | 250 | 0.40 | 78.8 | NA |
| | IV | 1 | 42.2 | NA | NA | 6090 | 0.17 | 236 | NA |
| | IV | 10 | 386 | NA | NA | 47100 | 0.21 | 247 | NA |
| | SC | 10 | NA | 106 | 72 | 33900 | 0.30 | 254 | 72 |
| anti-VHH detection | IV | 0.1 | 2.93 | NA | NA | 286 | 0.35 | 96.2 | NA |
| | IV | 1 | 35.1 | NA | NA | 4870 | 0.21 | 180 | NA |
| | IV | 10 | 282 | NA | NA | 41500 | 0.24 | 186 | NA |
| | SQ | 10 | NA | 117 | 48 | 34300 | 0.30 | 209 | 83 |

NOTE:
Parameters are reported as mean.

TABLE 14

Plasma Pharmacokinetic Parameters for Antibody II Following a Single 0.1 (N = 2), 1 (N = 2), or 10 mg/kg IV (N = 2) or 10 mg/kg SQ (N = 3) Dose to Cynomolgus Monkeys.

| ELISA Method | Route | Dose (mg/kg) | $C_0$ (µg/mL) | $C_{max}$ (µg/mL) | $T_{max}$ (hr) | $AUC_{0-inf}$ (hr*µg/mL) | CL or CL/F (mL/hr/kg) | $t_{1/2}$ (hr) | % F |
|---|---|---|---|---|---|---|---|---|---|
| anti-Fab detection | IV | 0.1 | 2.47 | NA | NA | 189 | 0.54 | 82.9 | NA |
| | IV | 1 | 25.9 | NA | NA | 3280 | 0.32 | 194 | NA |
| | IV | 10 | 263 | NA | NA | 46500 | 0.22 | 291 | NA |
| | SC | 10 | NA | 95.9 (12.7) | 112 (111) | 35600 (1760) | 0.28 (0.01) | 220 (64.3) | 76.6 |
| anti-VHH detection | IV | 0.1 | 2.28 | NA | NA | 190 | 0.53 | 77.4 | NA |
| | IV | 1 | 27.6 | NA | NA | 3620 | 0.29 | 224 | NA |
| | IV | 10 | 349 | NA | NA | 38100 | 0.26 | 218 | NA |
| | SQ | 10 | NA | 99.9 (16.8) | 64 (14) | 34300 (5460) | 0.30 (0.04) | 194 (23.9) | 90.0 |

NOTE:
Parameters are reported as mean (IV route) or mean (SD) (SQ route).

Listing of Sequences

SEQ ID NO: 1 HCDR1
AASGYTFSSYVMH

SEQ ID NO: 2 HCDR2.1
VTSYDGTHEY

SEQ ID NO: 3 HCDR3
ARENNWAPDY

SEQ ID NO: 4 LCDR1
RASQDISNSLA

SEQ ID NO: 5 LCDR2
YAAFSLQS

SEQ ID NO: 6 LCDR3
YQYYNYPSA

SEQ ID NO: 7 HCDR2.2
VTSYDGTHEL

SEQ ID NO: 8 HC Variable Region (VH1)
QVQLVESGGGVVQPGRSLRLSCAASGYTFSSYVMHWVRQAPGKGLEWVAVT
SYDGTHEYYADSVKGRFTISRDNSKNTLYLQMNSLRAEDTAVYYCARENNW
APDYWGQGTLVTVSS SEQ ID NO: 9 HC Variable Region (VH2)
QVQLVESGGGVVQPGRSLRLSCAASGYTFSSYVMHWVRQAPGKGLEWVAVT
SYDGTHELYADSVKGRFTISRDNSKNTLYLQMNSLRAEDTAVYYCARENNW
APDYWGQGTLVTVSS SEQ ID NO: 10 LC Variable Region (VL)
DIQMTQSPSSLSASVGDRVTITCRASQDISNSLAWYQQKPGKAPKRLIYAA
FSLQSGVPSRFSGSGSGTEFTLTISSLQPEDFATYYCYQYYNYPSAFGQGT
KLEIK SEQ ID NO: 11 Linker 1
DKTHTGGGGQGGGGQGGGGQGGGGQGGGGQ SEQ ID NO: 12 Linker 2
DKTGGGGQGGGGQGGGGQGGGGQGGGGQ SEQ ID NO: 13 Albumin-binding VHH
EVQLLESGGGLVQPGGSLRLSCAASGRYIDETAVAWFRQAPGKGREFVAGI
GGGVDITYYADSVKGRFTISRDNSKNTLYLQMNSLRPEDTAVYYCAARPGR
PLITSKVADLYPYWGQGTLVTVSSPP SEQ ID NO: 14 HC anti-Fab - albumin-binding VHH
Fusion 1
QVQLVESGGGVVQPGRSLRLSCAASGYTFSSYVMHWVRQAPGKGLEWVAVT
SYDGTHEYYADSVKGRFTISRDNSKNTLYLQMNSLRAEDTAVYYCARENNW
APDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNH
KPSNTKVDKKVEPKSCDKTHTGGGGQGGGGQGGGGQGGGGQGGGGQEVQLL
ESGGGLVQPGGSLRLSCAASGRYIDETAVAWFRQAPGKGREFVAGIGGGVD
ITYYADSVKGRFTISRDNSKNTLYLQMNSLRPEDTAVYYCAARPGRPLITS
KVADLYPYWGQGTLVTVSSPP SEQ ID NO: 15 HC anti-GITR Fab - albumin-binding
VHH Fusion 2
QVQLVESGGGVVQPGRSLRLSCAASGYTFSSYVMHWVRQAPGKGLEWVAVT
SYDGTHELYADSVKGRFTISRDNSKNTLYLQMNSLRAEDTAVYYCARENNW
APDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNH
KPSNTKVDKKVEPKSCDKTHTGGGGQGGGGQGGGGQGGGGQGGGGQEVQLL
ESGGGLVQPGGSLRLSCAASGRYIDETAVAWFRQAPGKGREFVAGIGGGVD
ITYYADSVKGRFTISRDNSKNTLYLQMNSLRPEDTAVYYCAARPGRPLITS
KVADLYPYWGQGTLVTVSSPP SEQ ID NO: 16 LC
DIQMTQSPSSLSASVGDRVTITCRASQDISNSLAWYQQKPGKAPKRLIYAA
FSLQSGVPSRFSGSGSGTEFTLTISSLQPEDFATYYCYQYYNYPSAFGQGT
KLEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC SEQ ID NO: 17 DNA Encoding HC anti-GITR Fab-
albumin-binding VHH Fusion 1
CAAGTGCAGCTCGTGGAGTCGGGTGGCGGAGTGGTGCAGCCCGGAAGGTCC
TTGCGGCTCTCCTGTGCCGCTTCCGGCTACACCTTCTCGAGCTACGTGATG
CACTGGGTCAGACAGGCACCGGGAAAGGGTCTGGAATGGGTGGCCGTGACT
TCCTACGACGGCACCCACGAGTATTACGCCGACTCAGTGAAGGGCCGCTTC
ACTATCTCCCGGGACAACTCAAAGAACACCCTGTATCTGCAAATGAACTCA
CTGCGGGCCGAGGACACTGCCGTGTACTACTGCGCGCGCGAAAACAACTGG
GCCCCTGACTACTGGGGACAGGGGACTCTGGTCACTGTGTCGTCCGCCTCG
ACCAAGGGACCCTCCGTGTTTCCGCTGGCGCCAAGCAGCAAGAGCACCTCG
GGGGGAACTGCAGCCTTGGGGTGCCTCGTGAAGGATTACTTCCCCGAACCA
GTGACCGTGTCCTGGAACTCTGGGGCCCTCACCAGTGGAGTGCACACTTTC
CCTGCGGTGCTGCAGTCCTCCGGACTGTACAGCCTGTCCAGCGTGGTCACG
GTGCCCAGCTCCTCACTGGGCACCCAGACCTACATTTGCAACGTGAACCAT
AAGCCGTCCAATACCAAAGTCGATAAGAAAGTCGAGCCGAAGTCCTGCGAC
AAGACACACACCGGTGGAGGAGGCCAGGGTGGAGGTGGACAAGGCGGCGGA
GGTCAAGGCGGAGGAGGACAGGGTGGC GGAGGACAGGAAGTGCAGCTGCT
GGAGTCCGGGGGCGGACTGGTGCAGCCTGGCGGATCATTGCGGCTGTCGTG
CGCGGCCTCCGGACGCTACATCGACGAGACAGCAGTGGCCTGGTTCAGACA
GGCTCCCGGAAAGGGAAGAGAGTTCGTGGCCGGAATTGGCGGGGAGTCGA
CATTACCTACTACGCCGATTCCGTGAAGGGTCGCTTTACCATCTCCCGGGA
CAATTCGAAGAACACCCTGTACCTCCAAATGAACTCGCTGAGGCCGGAAGA
TACCGCGGTGTATTACTGTGCCGCCCGCCCGGGACGCCCGCTGATCACGTC
CAAAGTCGCCGACCTGTACCCGTACTGGGGACAGGGTACCCTCGTGACCGT
GTCCAGCCCTCCC SEQ ID NO: 18 DNA Encoding HC GITR- and albumin-
binding VHH Fusion 2
CAGGTGCAGCTCGTGGAGTCGGGTGGCGGAGTGGTGCAGCCCGGAAGGTCC
TTGCGGCTCTCCTGTGCCGCTTCCGGCTACACCTTCTCGAGCTACGTGATG

Listing of Sequences

CACTGGGTCAGACAGGCACCAGGAAAGGGTCTGGAATGGGTGGCCGTGACC

TCCTACGACGGCACCCACGAGCTGTACGCCGACTCAGTGAAGGGCCGCTTC

ACTATCTCCCGGGACAACTCAAAGAACACCCTGTATCTGCAAATGAACTCA

CTGCGGGCCGAGGACACTGCCGTGTACTACTGCGCGCGCGAAAATAACTGG

GCCCCTGACTACTGGGGACAGGGGACTCTGGTCACTGTGTCGTCCGCCTCG

ACCAAGGGACCCTCCGTGTTTCCGCTGGCGCCAAGCAGCAAGAGCACCTCG

GGGGGAACTGCAGCCTTGGGGTGCCTCGTGAAGGATTACTTCCCCGAACCA

GTGACCGTGTCCTGGAACTCTGGGGCCCTCACCAGTGGAGTGCACACTTTC

CCTGCGGTGCTGCAGTCCTCCGGACTGTACGCCTGTCCAGCGTGGTCACG

GTGCCCAGCTCCTCACTGGGCACCCAGACCTACATTTGCAACGTGAACCAT

AAGCCGTCCAATACCAAAGTCGATAAGAAAGTCGAGCCGAAGTCCTGCGAC

AAGACACACACCGGTGGAGGAGGCCAGGGTGGAGGTGGACAAGGCGGCGGA

GGTCAAGGCGGAGGAGGACAGGGTGGCGGAGGACAGGAAGTGCAGCTGCTG

GAGTCCGGGGGCGGACTGGTGCAGCCTGGCGGATCATTGCGGCTGTCGTGC

GCGGCCTCCGGACGCTACATCGACGAGACAGCAGTGGCCTGGTTCAGACAG

GCTCCCGGAAAGGGAAGAGAGTTCGTGGCCGGAATTGGCGGGGAGTCGAC

ATTACCTACTACGCCGATTCCGTGAAGGGTCGCTTTACCATCTCCCGGGAC

AATTCGAAGAACACCCTGTACCTCCAAATGAACTCGCTGAGGCCGGAAGAT

ACCGCGGTGTATTACTGTGCCGCCCGCCCGGGACGCCCGCTGATCACGTCC

AAAGTCGCCGACCTGTACCCGTACTGGGGACAGGGTACCCTCGTGACCGTG

TCCAGCCCTCCC

SEQ ID NO: 19 DNA Encoding LC
GATATCCAGATGACCCAGTCCCCGAGCTCGCTGTCCGCTTCCGTGGGAGAC

AGAGTGACGATCACTTGTCGGGCCAGCCAAGACATTAGCAACTCCCTGGCC

TGGTACCAGCAGAAGCCCGGCAAAGCACCCAAGAGGTTGATCTACGCGGCC

TTTTCACTGCAATCCGGAGTGCCGAGCCGGTTCTCCGGATCCGGTTCAGGG

ACCGAGTTCACCTTGACCATTAGCAGCCTGCAGCCCGAAGATTTCGCCACT

TACTACTGCTACCAGTATTACAATTACCCATCGGCGTTCGGCCAAGGCACC

AAGCTCGAGATCAAGCGGACCGTGGCTGCACCATCTGTCTTCATCTTCCCG

CCATCTGATGAGCAGTTGAAATCTGGAACTGCCTCTGTTGTGTGCCTGCTG

AATAACTTCTATCCCAGAGAGGCCAAAGTACAGTGGAAGGTGGATAACGCC

CTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCC

GTCACAAAGAGCTTCAACAGGGGAGAGTGC

SEQ ID NO: 20 Human GITR Full-length (w/o signal peptide)
QRPTGGPGCGPGRLLLGTGTDARCCRVHTTRCCRDYPGEECCSEWDCMCVQ

PEFHCGDPCCTTCRHHPCPPGQGVQSQGKFSFGFQCIDCASGTFSGGHEGH

CKPWTDCTQFGFLTVFPGNKTHNAVCVPGSPPAEPLGWLTVVLLAVAACVL

LLTSAQLGLHIWQLRSQCMWPRETQLLLEVPPSTEDARSCQFPEEERGERS

AEEKGRLGDLWV

SEQ ID NO: 21 Human GITR ECD (w/o signal peptide)
QRPTGGPGCGPGRLLLGTGTDARCCRVHTTRCCRDYPGEECCSEWDCMCVQ

PEFHCGDPCCTTCRHHPCPPGQGVQSQGKFSFGFQCIDCASGTFSGGHEGH

CKPWTDCTQFGFLTVFPGNKTHNAVCVPGSPPAE

SEQ ID NO: 22: Signal Peptide amino acid sequence
METDTLLLWVLLLWVPGSTG

The invention claimed is:

1. A compound comprising X, wherein X is an antigen binding fragment that binds human GITR (SEQ ID NO: 20) and comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein
   i. the HCDR1 comprises SEQ ID NO: 1,
   ii. the HCDR2 comprises SEQ ID NO: 2 or SEQ ID NO: 7,
   iii. the HCDR3 comprises SEQ ID NO: 3,
   iv. the LCDR1 comprises SEQ ID NO: 4,
   v. the LCDR2 comprises SEQ ID NO: 5, and
   vi. the LCDR3 comprises SEQ ID NO: 6.

2. The compound of claim 1 having the formula:
X-L-M or M-L-X,
   wherein X is an antibody Fab fragment or an antibody Fab' fragment;
   wherein M is a VHH moiety that binds to human serum albumin; and
   wherein L (if present) is a linker.

3. The compound of claim 2, wherein the VHH moiety comprises SEQ ID NO: 13, or an amino acid sequence having at least 90% to 99% sequence similarity thereto.

4. The compound of claim 3, wherein the VHH moiety is fused to the C-terminus of the heavy chain first constant domain (CH1) of the Fab fragment via L.

5. The compound of claim 4, wherein X comprises a VL having SEQ ID NO: 10.

6. The compound of claim 5, wherein X comprises a VH having SEQ ID NO: 8 or a VH having SEQ ID NO: 9.

7. The compound of claim 6, wherein L comprises a peptide linker selected from the group consisting of SEQ ID NO: 11 and SEQ ID NO: 12.

8. The compound of claim 7, wherein X comprises a light chain (LC) as shown in SEQ ID NO: 16.

9. The compound of claim 8, wherein X comprises a HC as shown in SEQ ID NO: 14 or a HC as shown in SEQ ID NO: 15.

10. A pharmaceutical composition comprising the compound of claim 1, and a pharmaceutically acceptable excipient, diluent or carrier.

11. A method of treating arthritis, rheumatoid arthritis (RA), inflammatory bowel disease (IBD), Crohn's disease (CD) or ulcerative colitis (UC) in a subject in need thereof, comprising administering to the subject a therapeutically effective amount of the compound of claim 1.

12. A method of treating atopic dermatitis (AtD) in a subject in need thereof, comprising administering to the subject a therapeutically effective amount of the compound of claim 1.

13. A nucleic acid comprising SEQ ID NO: 17, SEQ ID NO: 18, or SEQ ID NO: 19.

14. A vector comprising the nucleic acid of claim 13.

15. A cell comprising the vector of claim 14.

16. A process of producing a compound comprising culturing the cell of claim 15 under conditions such that the antibody is expressed and recovering the expressed antibody from the culture medium.

17. A compound produced by the process of claim 16.

* * * * *